(12) United States Patent
Shibamoto

(10) Patent No.: US 6,205,841 B1
(45) Date of Patent: Mar. 27, 2001

(54) GAS CHROMATOGRAPH

(75) Inventor: Shigeaki Shibamoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/252,932

(22) Filed: Feb. 19, 1999

(30) Foreign Application Priority Data

Feb. 20, 1998 (JP) .................................................. 10-056144

(51) Int. Cl.$^7$ .......................... G01N 21/72; G01N 31/12; G01N 30/08
(52) U.S. Cl. .......................... 73/23.41; 356/315; 356/417; 436/122; 436/123; 436/119; 436/172; 436/171; 422/89; 422/91
(58) Field of Search .................................... 356/315, 417; 436/106, 123, 119, 122, 155, 158, 160, 161, 171, 172; 422/89, 83, 88, 91, 52; 73/23.35, 23.4, 23.41, 23.42

(56) References Cited

U.S. PATENT DOCUMENTS

| | | | |
|---|---|---|---|
| 3,661,533 | * | 5/1972 | David et al. ............................ 23/254 |
| 3,917,405 | * | 11/1975 | Hartmann et al. ...................... 356/87 |
| 4,119,404 | * | 10/1978 | Price ................................. 23/232 E |
| 4,167,334 | * | 9/1979 | Phillips ............................... 356/315 |
| 4,805,441 | * | 2/1989 | Sides et al. ........................... 73/23.1 |
| 5,014,541 | * | 5/1991 | Sides et al. ......................... 73/23.41 |

* cited by examiner

Primary Examiner—Hezron Williams
Assistant Examiner—Rose M. Miller
(74) Attorney, Agent, or Firm—Armstrong, Westerman, Hattori, McLeland & Naughton

(57) ABSTRACT

Mass flow controllers are respectively placed in the middle of a hydrogen gas tube and air tube connected to a FPD. The flow controllers are controlled to supply hydrogen and oxygen from the nozzle to achieve the optimum mixture rate of hydrogen and oxygen for combustion of each target component in a sample. Since the mixture rate of hydrogen gas and air is optimum for each target component, the quantity of light emitted by the combustion increases and detection of each target component improves.

11 Claims, 3 Drawing Sheets output of the first
photomultiplier tube output of the second
photomultiplier tube hydrogen-air
mixture rate

GAS CHROMATOGRAPH

BACKGROUND OF THE INVENTION

This invention relates to a gas chromatograph with a flame photometric detector (FPD). More specifically, this invention relates to the gas chromatograph with the FPD which detects, in just one analysis, plural components included in a sample, each component having a different light-emitting wavelength.

Various types of detectors of the gas chromatograph are made practicable. The FPD, one of these detectors, is a detector for selectively detecting a sulfur compound and a phosphorus compound. Therefore, the FPD is used for various purposes, such as for an analysis of offensive odor elements like hydrogen sulfide, methyl mercaptun and the like, the detection of a very small quantity of sulfur included in chemicals, an analysis of residual pesticide, an analysis of biochemical elements, and the like.

FIG.3 is a schematic diagram of a detection cell of a typical FPD. A sample gas tube 10 connected to a column outlet of a gas chromatograph, a hydrogen supply tube 11, and an air (or oxygen) supply tube 12 are connected to a nozzle 13 having a gas spouting outlet 14 directed upward. A transparent crystal cylinder 15 is placed around the nozzle 13. The whole of the crystal cylinder 15 is covered with a heat insulation block 16 made of metal. A heater and temperature sensor, not shown in the Figure, are embedded in or attached to the heat insulation block 16. According to a known feedback control of the heater using temperature information, the heat insulation block 16 is kept at a designated temperature. A designated part of the heat insulation block 16 is bored to define a detection window 17. A wavelength filter 19 is placed through a cooling fin 18 outside the detection window 17. Further outside the wavelength filter 19, a photomultiplier tube 20 as a detector is placed. The wavelength filter 19 is designed to transmit only the light with the target wavelength corresponding to the target sample component.

An operation principle of the above mentioned FPD is as follows. Carrier gas such as nitrogen gas supplied through the sample gas tube 10, hydrogen gas supplied through the hydrogen supply tube 11, and air supplied through the air supply tube 12 are mixed at the tip of the nozzle 13, then a hydrogen flame 21 is formed by combustion of this mixture. For example, when a sample component flowing out of the gas chromatograph column is introduced into the flame, it is combusted and the light having the target wavelength corresponding to the sample component is emitted. Especially, a reducing flame of peroxide emits the light with wavelengths of 394 $\mu$m and 526 $\mu$m through combustion of a sulfur compound and a phosphorus compound, respectively. The light emitted from a combustion part 22 for the sample component in the hydrogen flame 21 passes the transparent crystal cylinder 15 and reaches the wavelength filter 19. Only the light with the target wavelength selectively passes through the wavelength filter 19 and reaches the photomultiplier tube 20. By these steps, component detection with very high selectivity becomes possible. The crystal cylinder 15 is used for protecting the wavelength filter 19 from tarnishing over from steam or soot and the like produced by the hydrogen flame 21.

As mentioned above, in the FPD, the light of the target wavelength which is different depending on material of the target component such as phosphorus, sulfur, and tin is emitted. In the FPD, shown in FIG.3, the wavelength filter 19 has to be changed depending on each different target component in order to detect the different target components. Therefore, in this single filter type of FPD, it is impossible to detect, in one analysis, both a sulfur compound and a phosphorus compound which are separated in a column to exit from the column at different times. On the other hand, there is another type of FPD which has two different wavelength filters transmitting the light of the target wavelengths corresponding to two components, respectively, and two photomultiplier tubes detecting the light transmitted by the wavelength filters, respectively. In this dual filters type of FPD, a phosphorus compound and sulfur compound, which are separated in the column to exit at different times, are combusted in a hydrogen flame. The light with each of the target wavelengths corresponding to phosphorous and sulfur compounds emitted from the flame is selectively transmitted through a respective one of each of the wavelength filters, and each transmitted light is detected by a respective one of each of photomultiplier tubes.

In the FPD, shown in FIG.3, when a mixture rate of hydrogen gas and air changes, the size of the hydrogen flame 21 changes and also the temperature distribution in the flame changes. Since each mechanism for emission of light in sulfur, phosphorus, and tin, is different from the others, each mixture rate of hydrogen gas and air for maximizing a light amount emitted by combustion is also different depending on each component combusted. Therefore, it is desirable to set a proper flow amount of hydrogen and air supplied to the nozzle 13 depending on the target component in order to obtain a large amount of light and to enhance the detection. In the single filter type of FPD, shown in FIG.3, the most suitable combustion can be realized by changing the wavelength filter into a proper wavelength filter for the target component and resetting proper flow amounts of hydrogen gas and air depending on the target component.

On the other hand, when plural components are measured in one analysis (one sample injection) with the dual filters type of FPD, each flow amount of hydrogen gas and air is set so that a mixture rate of them becomes intermediate among the optimum mixture rates of those target components. In this case, since the combustion of the components is not optimum and each amount of light emitted is not maximum, the detection for each of the target components is not good.

SUMMARY OF THE INVENTION

This invention is achieved to solve the above problems. An object of this invention is to provide a gas chromatograph with a FPD which makes it possible to improve its detection by carrying out the optimum combustion for every target component in a hydrogen flame when plural components are measured in one analysis.

This invention is a gas chromatograph, with a flame photometric detector having a hydrogen flame formed by combusting a mixture of hydrogen and oxygen, a sample tube for introducing a sample to said flame, at least two different wavelength filters transmitting only the light with the target wavelengths corresponding two target components, respectively, at least two optical detectors detecting said light transmitted through said filters, respectively, a chromatographic column connected to the sample tube, in which each of the components included in the sample are separated, a hydrogen gas tube supplying said flame photometric detector with the hydrogen, a oxygen gas tube supplying said flame photometric detector with the oxygen, a first mass flow controller controlling a flow rate of said hydrogen, a second mass flow controller controlling a flow rate of said oxygen, and control means for controlling said first mass flow controller or/and second mass flow controller to change a mixture rate of the hydrogen gas and the oxygen timewise so that components introduced into said flame combusts most suitably, respectively.

When plural components in the sample are predetermined, the time when each of the components comes out of the column, which is called retention time, is predictable. Flow amounts of hydrogen gas and air or oxygen are set to the control means to be the most suitable mixture rate of them for combustion of the mixture, that is, for detection of each component. Each predicted the retention time when each component comes out is also set to the control means. Through the analysis, the control means controls the first and second flow controller based on the mixture rates and the predicted retention times set in advance. According to these controls, for example, when a phosphorus compound comes out of the column, the mixture rate becomes most suitable for combustion of phosphorus and a larger light amount from the phosphorus combustion is obtained. When a sulfur compound comes out of the column, the mixture rate also becomes most suitable for combustion of sulfur and a larger light amount from the sulfur combustion is obtained.

According to the gas chromatograph of this invention, since the most suitable combustion is carried out for every target component included in the sample, a larger light amount for each target component from the combustion is obtained. Therefore, even though only one analysis is carried out for plural components, since the signal level corresponding to each target component detected by the optical sensor increases, the detection for each component improves.

DETAILED DESCRIPTION OF THE PREFERRED EMBODIMENT

Figure 1:
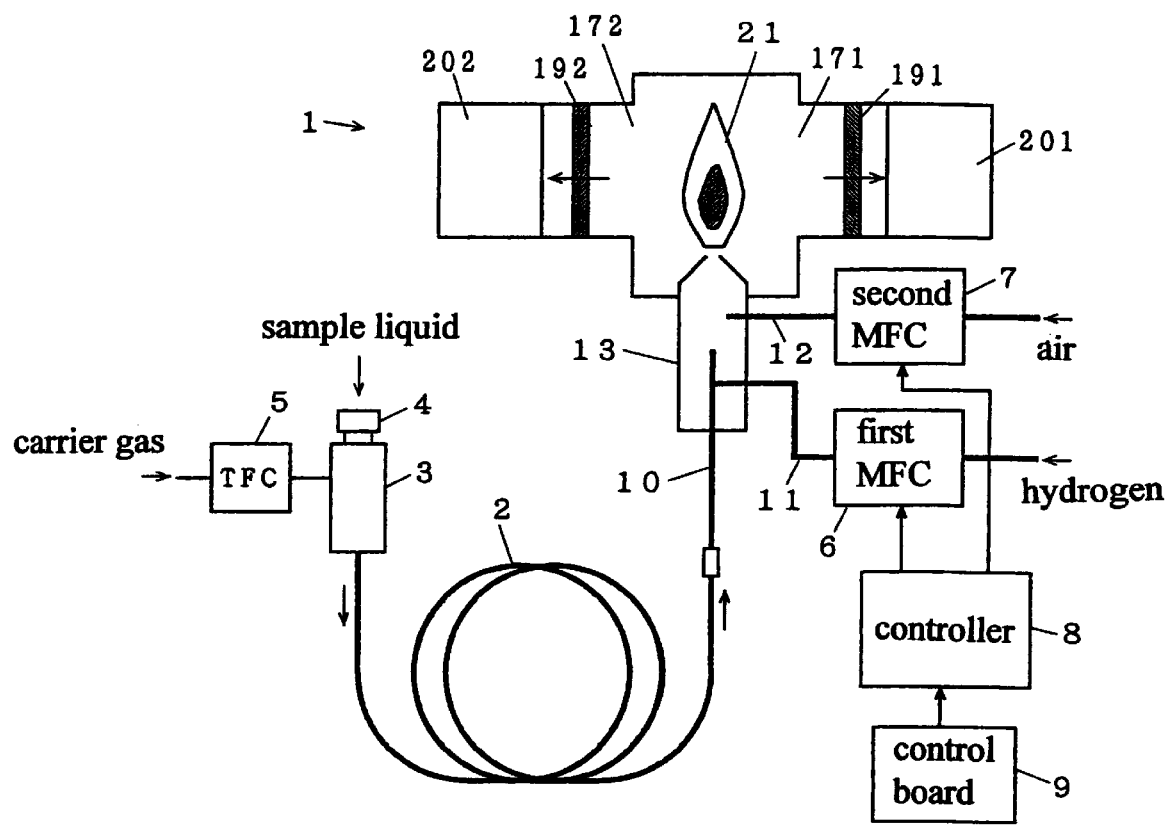
FIG. 1 is a schematic diagram showing a gas chromatograph of a preferred embodiment of this invention.
Figure 2:
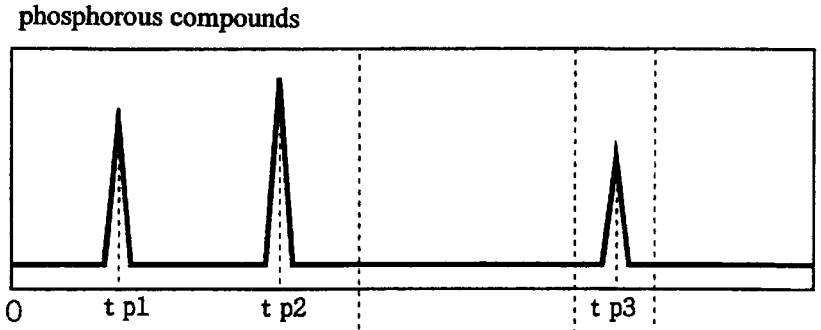
FIGS. 2 (a)–(c) are drawings used for explaining an operation of the gas chromatograph
Figure 2:
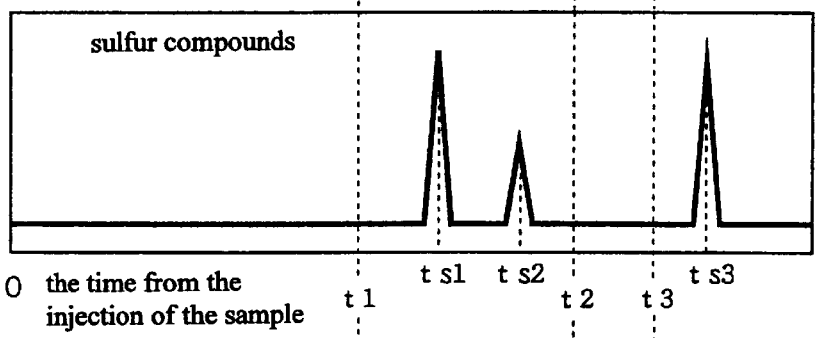
Figure 2:
Figure 3:
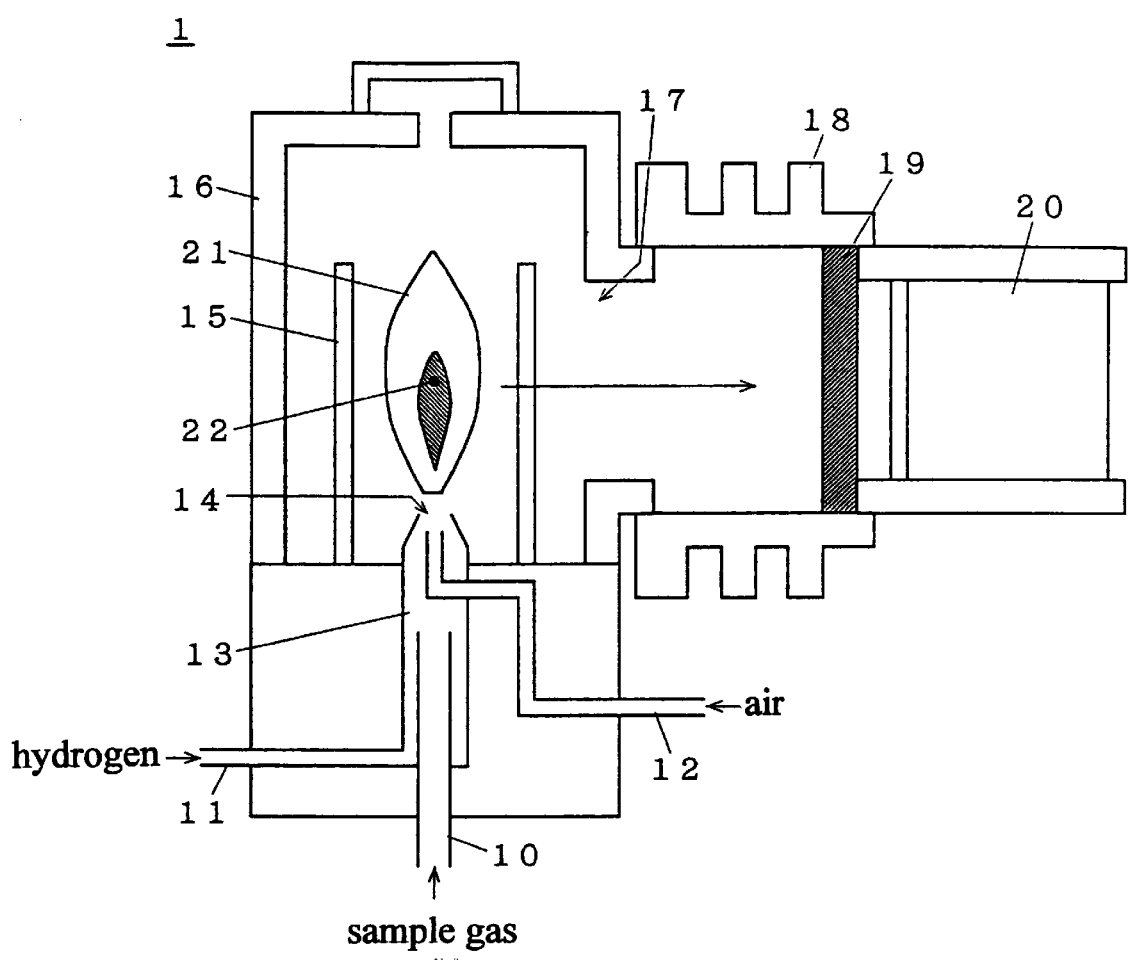
FIG. 3 is a schematic diagram showing a typical flame photometric detector.

The following is a detailed description of a gas chromatograph of a preferred embodiment of the present invention, with reference to FIGS. 1, 2(a), 2(b) and 2(c). FIG. 1 shows a schematic drawing of the gas chromatograph. FIGS.2 (a) and (b) show chromatograms based on detection signals of a first and second photomultiplier tubes 201, 202 shown in FIG. 1, respectively. FIG. 2(c) shows mixture rates of hydrogen gas and air at a FPD (Frame Photometric Detector). In FIG. 1, the same symbols are used for the same or corresponding elements described above in the typical FPD shown in FIG. 3. The detailed structure around and in a nozzle 13 in FIG. 1 is the same as that shown in FIG.3.

As shown in FIG. 1, one end of a sample gas tube 10 is connected to a detection cell 1 of the FPD and the other end thereof is connected to an outlet of a gas chromatograph column 2. An injection chamber 3 is placed at an inlet of the column 2. Carrier gas such as Helium is provided to the injection chamber 3 through a total flow controller (TFC) 5. A designated amount of sample liquid is also injected by a syringe, not shown in the drawings, into the injection chamber 3 through a septum 4 placed at the upper part thereof. Although not shown in the drawings, a purge flow channel for discharging undesired gas that the septum 4 generates and a sprit flow channel for discharging part of the carrier gas and evaporated sample are connected to the injection chamber 3 as the occasion demands.

The detection cell 1 of the FPD has two opposite detection windows 171, 172 at the sides of a hydrogen flame 21, respectively. Further outside of them, first and second wavelength filters 191, 192 are placed. These filters 191, 192 transmit the target wavelengths corresponding to the target components, respectively. The first and second photomultiplier tubes 201, 202 are also placed corresponding to the filters 191, 192, respectively. For example, the first wavelength filter 191 has the characteristic of transmitting the light with the wavelength in the neighborhood of 526 $\mu$m corresponding to a phosphorous compound. The second filter 192 has the characteristic of transmitting the light with the wavelength in the neighborhood of 394 $\mu$m corresponding to a sulfur compound. In this embodiment, the first and second wavelength filters 191 and 192 are placed immediately in front of the first and second photomultiplier tubes 201, 202, respectively. This invention may also employ a structure for condensing each of the light transmitted through the wavelength filters 191, 192 and leading each of these lights to the photomultiplier tubes 201, 202 such as through optical fibers and the like. This invention may also employ a structure for taking out light emitted by combustion in the hydrogen flame 21, such as by optical fibers and the like and introducing the light to the wavelength filters 191, 192 placed outside through the optical fibers.

A first and second mass flow controllers (MFC) 6, 7 are connected to the hydrogen gas tube 11 and the air tube 12 in the middle of them, respectively. Control signal lines connect a controller 8 with the mass flow controllers 6, 7. The controller 8 instructs flow amounts to the mass flow controller 6, 7 through these signal lines. A control board 9 is established in the controller 8. An operator can set various analysis conditions necessary for a chromatograph analysis for the controller 8 through the control board 9. The controller 8 controls a timing for injecting the sample liquid into the injection chamber 3, rise in temperature of the column 2, a flow amount of carrier gas, and the like based on the analysis conditions set through the control board 9, besides the flow controls on the first and second mass flow controllers 6, 7.

The following is an explanation of an operation of the chromatograph shown in FIG. 1 when a sample having plural phosphorus compounds and sulfur compounds is analyzed. Before starting the analysis, an operator inputs to the controller 8, designated parameters and conditions (the size of the column 2, a carrier gas flow amount, heat-up program for the column, and the like) necessary for the analysis through the control board 9. The operator also provides a control program in the controller 8 with necessary parameters such as predicted retention times of the phosphorous compounds and sulfur compounds for controlling the mass flow controllers 6,7 to obtain the designated mixture rate of hydrogen and an air for every target component. The operator may also load an control program including the necessary parameters from an memory medium such as an optical disk instead of manually setting the necessary parameters.

As shown in FIGS. 2(a)–(c), we assume for example purpose only that the retention times of three kinds of phosphorus compounds, the first to the third phosphorus compounds, in a sample are tp1, tp2, and tp3, respectively. We also assume that the retention times of three kinds of sulfur compounds, the first to the third phosphorus compounds, in a sample are ts1, ts2, and ts3, respectively, and there is a relation of tp1<tp2<ts1<ts2<tp3<ts3. In this case, t1, t2, and t3 are determined to divide the time t from the injection of the sample into the following four terms (1)–(4):
(1) 0–t1 (tp2<t1<ts1)
(2) t1–t2 (ts2<t2<tp3)
(3) t2–t3 (tp3<t3<ts3)
(4) after t3.

As shown in FIG.2 (c), hydrogen gas and air flow amounts are set to be the most suitable mixture rate A for combustion of phosphorus compounds in the first term (1) and the third term (3). Hydrogen gas and air flow amounts are set to be the most suitable mixture rate B for combustion of sulfur compounds in the second term (2) and the fourth term (4).

Before injection of the sample liquid, the controller 8 controls the total flow controller 5 to keep the carrier gas flow at a fixed rate in the column 2 through the injection chamber 3. For the analysis, the sample liquid is injected into the injection chamber 3. The sample evaporated in the injection chamber 3 is carried by the carrier gas into the column 2. The components in the evaporated sample separates when passing through the column 2 so as to exit from the column at different times. The controller 8 instructs the first and second mass flow controller 6,7 to achieve the preset flow amounts (mixture rate A) for the first term (1).

The first phosphorus compound comes out from the column 2 around the time tp1 from the injection of the sample and is introduced into the hydrogen flame 21. At that time, since a mixture rate of hydrogen gas and air is most suitable (mixture rate A), the first phosphorus compound combusts very well. A good quantity of the light emitted by this combustion reaches the photomultiplier tube 201 through the first wavelength filter 191. Next, the second phosphorus compound is introduced into the hydrogen flame 21 around the time tp2 from the injection of the sample. At this time, since a mixture rate of hydrogen gas and air is still kept to be the mixture rate A, the second phosphorus compound also combusts very well. A good quantity of the light emitted by this combustion reaches the first photomultiplier tube 201 through the first wavelength filter 191.

When the time t from the injection of the sample reaches the time t1, the controller 8 instructs the first and second mass flow controllers 6,7 to achieve the preset flow amounts (mixture rate B) for the second term (2). Therefore, a mixture rate changes from the rate A to the rate B, as shown in FIG. 2(c). The first sulfur compound comes out from the column 2 around about the time ts1 from the injection of the sample and it is introduced into the hydrogen flame 21. At that time, since a mixture rate of hydrogen gas and air is most suitable (mixture rate B) for sulfur compounds, the first sulfur compound combusts very well. A good quantity of the light emitted by this combustion reaches the second photomultiplier tube 202 through the second wavelength filter 192. Next, the second sulfur compound is introduced into the hydrogen flame 21 around the time ts2 from the injection of the sample. At this time, since a mixture rate of hydrogen gas and air is still kept to be the mixture rate B, the second sulfur compound also combusts very well. A good quantity of the light emitted by this combustion reaches the second photomultiplier tube 202 through the second wavelength filter 192. In the same way, at the time t2 and t3 from the injection of the sample, the controller 8 instructs the first and second mass flow controller 6,7 to achieve the preset flow amount (mixture rate A) for the third term (3) and the preset flow amount (mixture rate B) for the fourth term (4), respectively. Therefore, the third phosphorus compound comes out around the time tp3 from the injection of the sample, a mixture rate of hydrogen gas and air is kept to be the mixture rate A which is most suitable for phosphorus. Also, the third sulfur compound comes out around the time ts3 from the injection of the sample, a mixture rate of hydrogen gas and air is kept to be the mixture rate B which is most suitable for sulfur.

Since the largest amount of light is emitted every time each component combusts, each signal peak of the phosphorus compounds and each signal peak of the sulfur compounds becomes very high. In the conventional analysis, when arranged to obtain the highest signal peak of phosphorus compounds, the signal peak of a sulfur compound becomes low. In addition, when the conventional art is arranged to obtain the highest signal peak of sulfur compounds, the signal peak of a phosphorus compound becomes low. In contrast, the gas chromatgraph of this embodiment makes it possible to obtain the highest signal peaks of both phosphorus and sulfur compounds and to improve the detection of all the components in a single analysis.

In case of analyzing another component detectable by the FPD such as tin, a wavelength filter which transmits the target wavelength light emitted by the combustion of tin is prepared and a flow amount of hydrogen and air which makes the most suitable combustion of tin in a hydrogen flame is set.

A preferred embodiment was described above. However, it should be understood that this invention covers all change and modification apparent to one skilled in the art without departing from essential characteristic thereof.

This application claims priority to Japanese Patent Application No. H10-56144 filed on Feb. 20, 1998, each disclosure of which is incorporated by reference in its entirely.

What is claimed is:

1. A gas chromatograph comprising:
   a flame photometric detector having;
      a hydrogen flame formed by combusting a mixture of hydrogen and oxygen,
      a sample tube for introducing a sample to said flame,
      at least two different wavelength filters transmitting only the light with target wavelengths corresponding to respective target components of said sample,
      at least two optical detectors detecting said light transmitted through said filters, respectively,
   a chromatographic column, connected to said sample tube, each of said target components included in said sample being separated during passage through said column;
   a hydrogen gas tube supplying said flame photometric detector with said hydrogen;
   an oxygen gas tube supplying said flame photometric detector with said oxygen;
   a first mass flow controller controlling a flow rate of said hydrogen;
   a second mass flow controller controlling a flow rate of said oxygen; and
   control means for controlling at least one of said first mass flow controller and said second mass flow controller to achieve different optimum mixture rates of said hydrogen and said oxygen for combustion of each of said components in said sample.

2. A gas chromatograph according to claim 1, further comprising an injection chamber connected to an inlet of said column, and evaporating said sample.

3. A gas chromatograph according to claim 2, further comprising:
 a carrier gas tube supplying carrier gas to said chamber; and
 a total flow controller controlling a flow rate of said carrier gas.

4. A gas chromatograph according to claim 2, wherein said chamber having a septum at upper part thereof.

5. A gas chromatograph according to claim 4, further comprising a purge flow channel connected to said chamber and discharging undesired gas generated from said septum.

6. A gas chromatograph according to claim 2, further comprising a split channel connected to said chamber and discharging said carrier gas and part of said evaporated sample.

7. A gas chromatograph according to claim 1, further comprising a detection cell surrounding said flame, said cell having two opposite detection windows on opposite sides across said flame,
 wherein said wavelength filters are placed outside said windows, respectively.

8. A gas chromatograph according to claim 1, wherein one of said filters transmits light with a wavelength of a phosphorous compound.

9. A gas chromatograph according to claim 1, wherein one of said filters transmits light with a wavelength of a sulfur compound.

10. A gas chromatograph according to claim 1, wherein said control means controls at least one of said first mass flow controller and said second mass flow controller to achieve the optimum mixture rate of hydrogen gas and oxygen gas for combustion of each of said target components for a period of time including a preset retention time for each of said target components.

11. A gas chromatograph according to claim 1, wherein said control means arranges preset retention times for a plurality of target compounds in said target components in time order, grouping into plural terms said retention times that are sequential and that corresponds to a subset of said plurality of compounds belonging to a same component, controlling at least one of said first mass flow controller and second mass flow controller to achieve the optimum rate of hydrogen gas and oxygen gas for combustion of each of said target components for said term related to each of said target components.

* * * * *